United States Patent
Buser et al.

[11] Patent Number: 6,120,292
[45] Date of Patent: Sep. 19, 2000

[54] HEALING CAP FOR DENTAL IMPLANTS

[75] Inventors: Daniel Buser, Muri; Alex Schär, Riehen, both of Switzerland

[73] Assignee: Institut Straumann AG, Waldenburg, Switzerland

[21] Appl. No.: 09/077,421

[22] PCT Filed: Dec. 3, 1996

[86] PCT No.: PCT/CH96/00426

§ 371 Date: May 27, 1998

§ 102(e) Date: May 27, 1998

[87] PCT Pub. No.: WO97/20518

PCT Pub. Date: Jun. 12, 1997

[30] Foreign Application Priority Data

Dec. 4, 1995 [CH] Switzerland ............... 3417/95

[51] Int. Cl.[7] ............................................. A61C 8/00
[52] U.S. Cl. ................................... 433/173; 433/172
[58] Field of Search .................................. 433/172, 173, 433/174, 175, 176

[56] References Cited

U.S. PATENT DOCUMENTS

| | | | |
|---|---|---|---|
| 4,856,994 | 8/1989 | Lazzara et al. | 433/173 |
| 5,026,285 | 6/1991 | Durr et al. | 433/173 |
| 5,145,372 | 9/1992 | Daftary et al. | 433/174 |
| 5,338,196 | 8/1994 | Beaty et al. | 433/172 |
| 5,368,160 | 11/1994 | Leuschen et al. | 433/174 |
| 5,368,483 | 11/1994 | Sutter et al. | 433/173 |
| 5,527,183 | 6/1996 | O'Brien | 433/173 |
| 5,622,500 | 4/1997 | Niznick | 433/173 |
| 5,755,575 | 5/1998 | Biggs | 433/174 |

FOREIGN PATENT DOCUMENTS

| | | |
|---|---|---|
| 0423798 | 4/1991 | European Pat. Off. . |
| 0630621 | 12/1994 | European Pat. Off. . |

OTHER PUBLICATIONS

Internationales Journal für Paradontologie & Restaurative Zahnheilkunde, special reprint, vol. 13, Issue 5, 1993, pp. 394–397 and 414.

The Emergence Profile System ™, 3i Implant Innovations, Inc. brochure, 1993.

Orale Implantologie, Georg Thieme Verlag Stuttgart, New York, 2nd Ed., 1994, pp. 308–311.

"Managing the Soft Tissue Margin: The Key to Implant Aesthetics," *Practical Periodontics and Aesthetic Dentistry*, vol. 5, No. 5, Jun./Jul. 1993, pp. 81–87.

*Primary Examiner*—John J. Wilson
*Attorney, Agent, or Firm*—Selitto & Associates

[57] ABSTRACT

A healing cap (100) is distinguished by a bevel (116), particularly in the region to be positioned labially, the bevel being advantageous for conditioning the soft parts, as well as a firm bearing on the associated implant (1), which is achieved by means of a mating shoulder (115) and an adaptable end portion (121) of a pin (120) or a centering bead. An occlusally applicable screw (200) can be mounted in the healing cap (100) beforehand, making it easier to handle. A special protective cap is provided as an intermediate treatment and as a temporary sealing element.

9 Claims, 4 Drawing Sheets

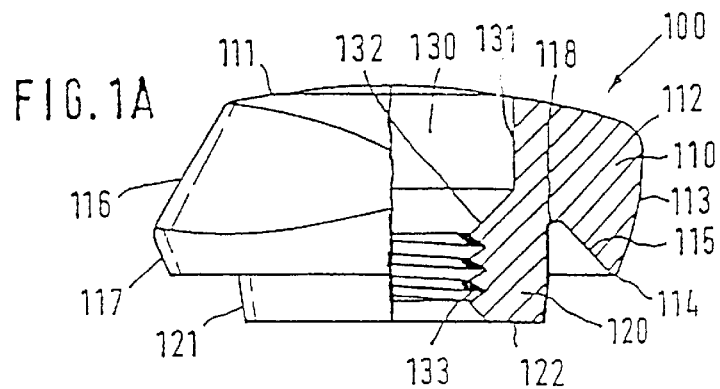
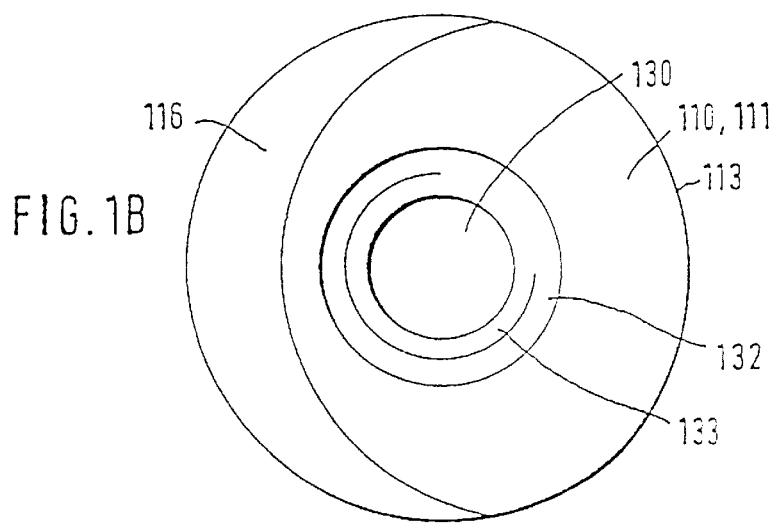
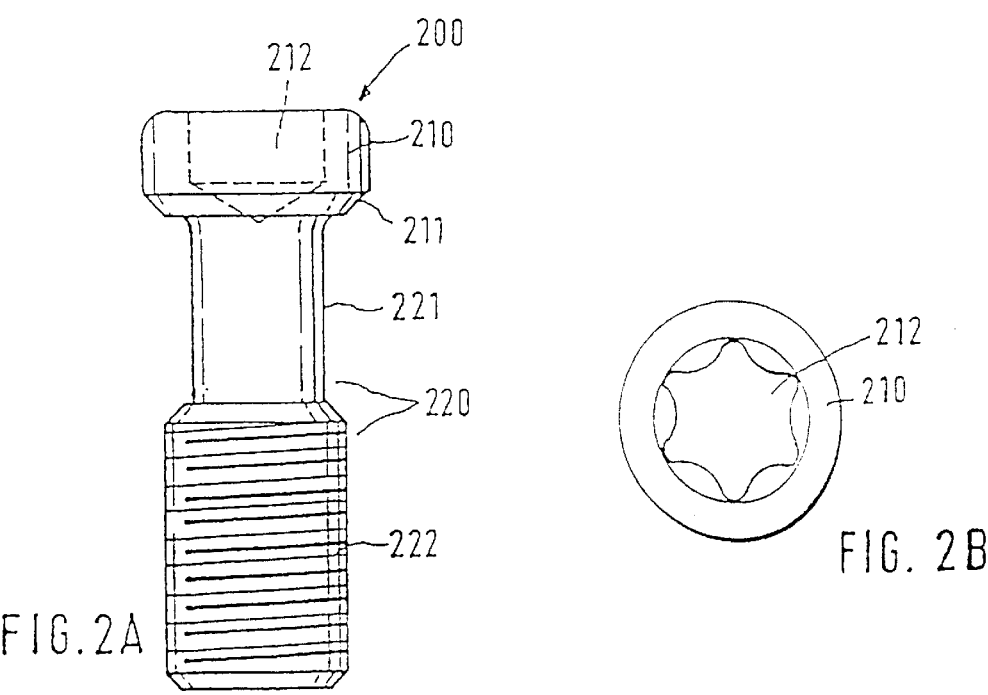

HEALING CAP FOR DENTAL IMPLANTS

APPLICATION AREA OF THE INVENTION

The invention relates to a healing cap which can be fixed on an intraossally positioned dental implant and has a mating shoulder which can be matched to the shoulder of the implant and which lies below the roof part of the healing cap. Furthermore, the invention comprises an occlusally applicable screw for fixing the healing cap on the implant, as well as a protective cap as a temporary provision following removal of the healing cap for sealing and protecting the implant.

When inserting an implant into the maxilla or the mandibula, the surgical procedure of intra-ossal implantation in principle ends with the positioning of a special healing cap, before the papillae and the gingiva are repositioned as precisely as possible and are adapted using sutures. These healing caps, which generally consist of a biocompatible material, extend the implant, during the healing phase, which lasts a number of months, as far as the surface of the soft tissue. This thus achieves transgingival healing, even though the shoulder of the implant is located subgingivally. Such an insertion depth of the implant is desirable particularly in the case of aesthetic reconstructions, in order that later no implant surface whatsoever remains visible.

In addition to the biocompatibility, healing caps also have to meet requirements with respect to perfect seating, which is as far as possible free of gaps, on the implant, to the protection of the head of the implant, to the shaping of the mucosa and to ease of handling in practice.

PRIOR ART

Single-part healing caps are known for temporarily sealing ITI® implants—the latter have an implant head which widens upwards in the form of a funnel and an uppermost, radially encircling implant shoulder with a bevel angle of 45°. Healing caps of this kind have a head part which is in principle cylindrical and flat and which on the side facing the implant has a hollow which complements the shoulder of the implant. On the top side, there is an engagement contour for a screwdriver, while a threaded pin extends below the top part, which pin can be screwed into the axial inside bore in the implant. If the availability of space requires the use of a healing cap with a smaller head, then a healing cap whose head can be countersunk in the inside cone of the implant is also available. Cf. the illustrations in: Internationales Journal für Paradontologie & Restaurative Zahnheilkunde [International Journal for Periodontology & Reconstructional Dentistry], reprint, Vol. 13, Issue 5, 1993, pages 397 and 414.

The healing caps mentioned to this extent have the drawback that, due to their contour, they do not contribute optimally to preforming the gingiva, and are felt by the patient to be intrusive, particularly in the anterior and posterior regions; the healing caps with a reduced head no longer protect the shoulder of the implant.

Single-part healing caps are also proposed in EP-0,423,798 B1, in the company publication: 3i® IMPLANT INNOVATIONS®—The Emergence Profile System®, 1993, and in PRACTICAL PERIODONTICS AND AESTHETIC DENTISTRY, Vol. 5 No. 5, June/July 1993. Although these healing caps may sometimes have a positive effect on the preforming of the gingiva, no improvement is achieved in the vestibular region. In addition, these healing caps are generally not suitable for implants with a bevelled shoulder.

Furthermore, two-part healing caps are known, which comprise the healing cap itself and an occlusally applied screw, which can be introduced into the cap head from above and is countersunk therein (referred to below simply as occlusal screw). The occlusal screw penetrates the healing cap centrally and axially, is supported therein, likewise engages in the inside bore provided in the implant and thus presses the healing cap onto the shoulder of the implant. Cf. the illustrations in Schroeder/Sutter/Buser/Krekeler: Orale Implantologie. [Oral Implantology] Georg Thieme Verlag Stuttgart, New York, 2nd Ed., 1994, pages 309f. In addition to the abovementioned disadvantages, these healing caps are extremely tricky to handle, in view of the two small parts—the healing cap and the occlusal screw put in separately.

OBJECT OF THE INVENTION

To summarize, it can thus be established that all of the healing caps known to date cannot be regarded as optimal. The problem underlying the invention is therefore to provide a healing cap which is distinguished by a firm seating on the implant, advantageous preforming of and bearing on the gingiva, aesthetically satisfactory contouring and manipulation of the papillae—particularly in the noticeable region of the front teeth—and by unproblematical handling.

SUMMARY OF THE INVENTION

The design principle of the proposed healing cap, which can be fixed flush on the implant, consists in providing on its roof part a bevel which is to be positioned labially and is partly to completely encircling. On the underside, the healing cap has a radially extending recess, so that a mating shoulder which is complementary to the shoulder of the implant is formed. An axially extending, conical pin is provided below the roof part, which pin is complementary to the upper part of the inside bore in the implant. In a preferred embodiment, a threaded bore for receiving an occlusal screw extends axially through the healing cap. The occlusal screw has a screw head which can be countersunk in the top surface of the healing cap and has an inner contour for the attachment of a turning tool. The screw shank, which at the start has a threaded part and near the screw head has a smooth shank part of reduced diameter, runs from the screw head.

For the period after the healing phase, that is to say between the impression-taking and the fabrication of the crown, a protective cap which can be fixed on the implant and rests on the shoulder of the implant is proposed for the purpose of replacing the healing cap. This protective cap is cylindrical and can be ground as desired, or it is bevelled and anatomically preformed such that the rough contour of a tooth is at least approximately produced. The protective cap is used as a simple temporary provision for closing the gap between the teeth and for protecting the emergent profile of the gingiva, the shoulder of the implant and the inserted secondary part.

The invention now provides a healing cap by means of which the gingiva is shaped into a position which appears natural, i.e. the surrounding soft parts are aesthetically conditioned. Furthermore, the healing cap ensures a firm seating which is as far as possible free of gaps on the implant, and significantly improved handling is provided. When using an occlusal screw, the latter is screwed into the healing cap before the latter is inserted, so that in principle only one part has to be handled. The unthreaded shank part on the occlusal screw allows the latter to be screwed tight freely, without concomitant rotation of the protective cap, since, when the occlusal screw is turned in relatively deeply, the external thread of the screw shank becomes disengaged from the internal thread situated in the healing cap.

BRIEF DESCRIPTION OF THE DRAWINGS

An exemplary embodiment of the healing cap according to the invention, with associated occlusal screw and protective cap, will be described in detail below with reference to the appended drawings, with possible modifications being mentioned at the end. In the drawings:

FIG. 1A: shows a front view in partial cross section of the healing cap;

FIG. 1B: shows a top view of FIG. 1A;

FIG. 2A: shows a front view of the occlusal screw;

FIG. 2B: shows a top view of FIG. 2A;

DETAILED DESCRIPTION OF AN EXEMPLARY EMBODIMENT

FIGS. 1A and 1B

At the top, the healing cap 100 has a roof part 110 which in principle is cylindrical and mushroom-shaped and a pin 120 which begins centrally on the underside of the roof part 110. A through-bore 130 extends axially through the healing cap 100.

Figure 3A:
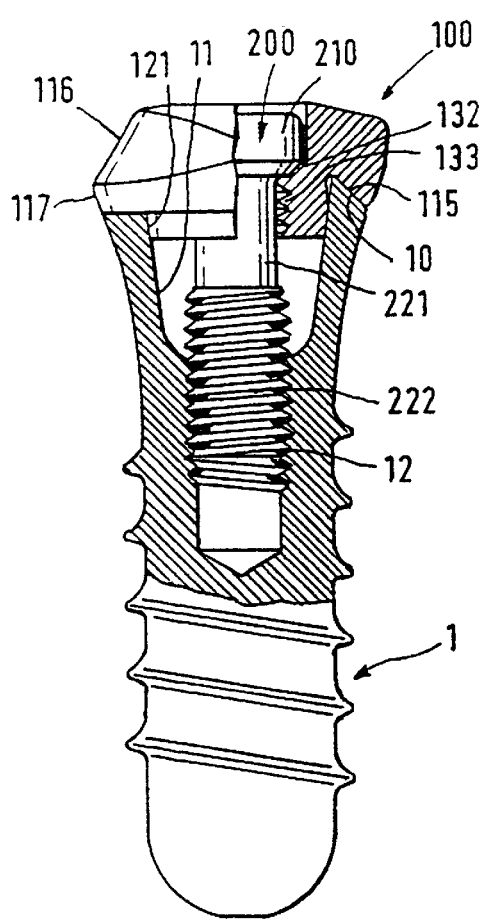
FIG. 3A: shows a full screw implant in partial cross section with an attached healing cap which is fixed by an occlusal screw.
Figure 3B:
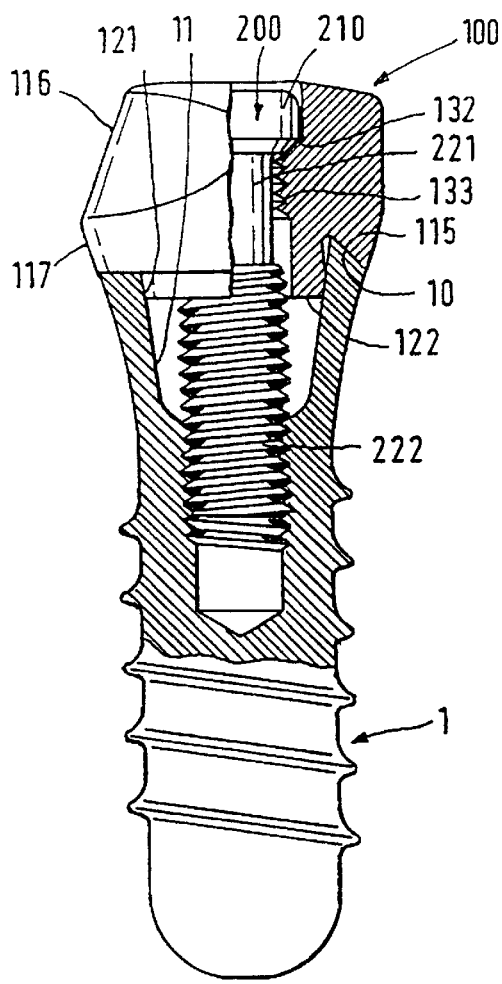
FIG. 3B: shows the representation of FIG. 3A with a higher healing cap.

The top surface 111 of the roof part 110 is slightly convex and the transition 112 to the outer, circumferential surface 113 is rounded off. The circumferential surface 113 is likewise convex and leads into the circular shoulder edge 114. From the shoulder edge 114 towards the pin 120, there exists a conical surface in the form of a circular ring, which forms the complementary mating shoulder 115 for the shoulder 10 of the implant (cf. FIGS. 3A and 3B). In the labially positioned region, a bevel 116, which starts at the top surface 111, is provided on the circumferential surface 113. The bevel 116 extends over approximately half the circumferential surface 113, tapers smoothly downwards and ends before reaching the shoulder edge 114, so that a partial chamfer 117 is formed.

The pin 120, at its lower portion 121, is adapted to the inside contour of the implant 1, i.e. it tapers conically. This conicity matches the inside cone 11 of the implant 1 (cf. FIGS. 3A and 3B).

The through-bore 130 has a plurality of different sections. Starting from the top surface 111, a screw-head receiving part 131 with a lower conical seat 132 is provided, on which the complementary cone base 211 of the screw head 210 of the occlusal screw 200 is supported (cf. FIG. 2A). An internally threaded section 133, which is of reduced diameter with respect to the screw head receiving part 131 and opens out on the underside 122 of the pin 120, extends downwards from the conical seat 132.

The following stipulation applies to the whole of the rest of the description. If, for the purpose of unambiguous representation, reference numerals are included in a figure but are not explained in the directly associated text of the description, reference is made to where they have been mentioned in preceding descriptions of figures.

FIGS. 2A and 2B

At the top, the occlusal screw 200 has the thickened screw head 210, on the upper side of which an engagement contour 212 for a complementary turning tool is provided. The conical base 211 corresponding to the conical seat 132 is situated on the underside of the screw head 210. The screw shank 220, which is divided into a smooth shank part 221 and into a threaded part 222, extends axially downwards from the screw head 210. The shank part 221 adjoins the conical base 211 and is in turn adjoined by the threaded part 222, which has a wider diameter than the smooth shank part 221 and a reduced diameter compared to the screw head 210.

FIG. 3A

The healing cap 100 is placed on the implant 1—in this case a full screw implant—and fixed by means of an occlusal screw 200. The mating shoulder 115 of the healing cap 100 is seated on the shoulder 10 of the implant. The screw head 210 is supported in the through-bore 130 on the conical seat 132, and the threaded part 222 of the occlusal screw 200 engages the internal thread 12 situated in the implant 1. The conical portion 121 of the pin 120 fits into the inside cone 11 in the implant 1 and thus centers the healing cap 100 on the implant 1.

FIG. 3B

For certain anatomical features or for an implant 1 which is positioned more deeply, a healing cap 100 with a higher roof part 110 is available. The bevel 116 and the length of the through-bore 130 are enlarged accordingly. It is also possible to allow the internally threaded section 133 in the healing cap 100 to end before emerging from the underside 122, the bottom section of the through-bore 130 then being smooth.

FIGS. 4A to 4D

As a rule, following an healing phase of about seven weeks, the healing cap 100 according to the invention is replaced by a conventional healing cap, in order to provide further conditioning of the gums. Impression-taking can be carried out after the end of the entire healing phase. A protective cap 300, 400 is provided as a temporary provision for filling the gap between the teeth or the sulcus and as a protection for the shoulder 10 of the implant.

Figure 4A:
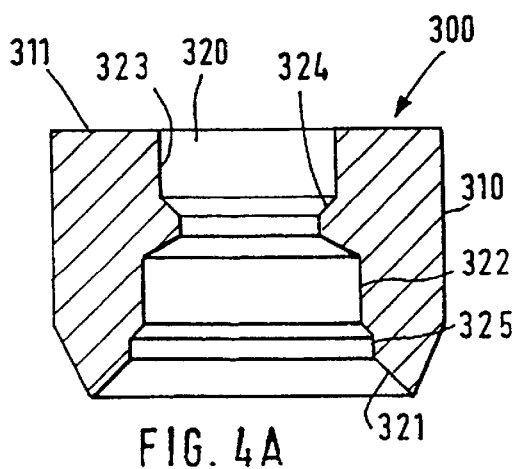
FIG. 4A: shows a sectional representation of a cylindrical embodiment of the protective cap.
Figure 4B:
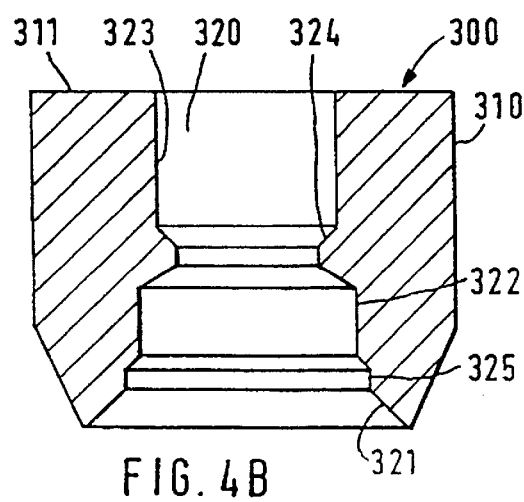
FIG. 4B: shows the protective cap of FIG. 4A in a higher form with increased diameter.

FIGS. 4A and 4B

In a first embodiment, the protective cap 300 comprises a cylindrical basic body 310, the upper side 311 in the form of a circular disc facing away from the tooth root and the lower part tapering conically. A through-bore 320 with a plurality of sections extends axially through the basic body 310. Towards the apical opening of the through-bore 320, the latter widens conically, in order to form a mating shoulder 321 which is complementary to the shoulder 10 of the implant. Adjoining the mating shoulder 321, there rises a short cylindrical section 325, which merges into a cylindrical section 322 of reduced diameter, above which is situated the screw head receiving part 323 with the conical seat 324. Depending on the spatial conditions in the mouth of the patient, protective caps 300 of different heights and diameters can be prefabricated. In order to insert the protective cap 300 into the patient's teeth such that it fits as well as possible, the cap can be ground as desired.

Figure 4C:
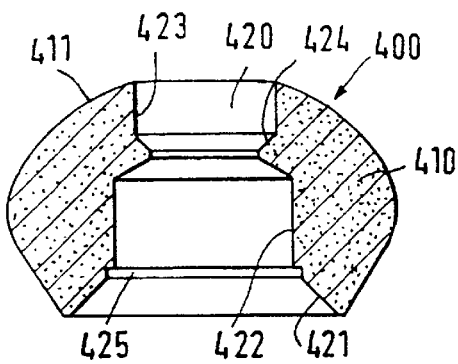
FIG. 4C: shows a sectional representation of a hemispherical configuration of the protective cap.
Figure 4D:
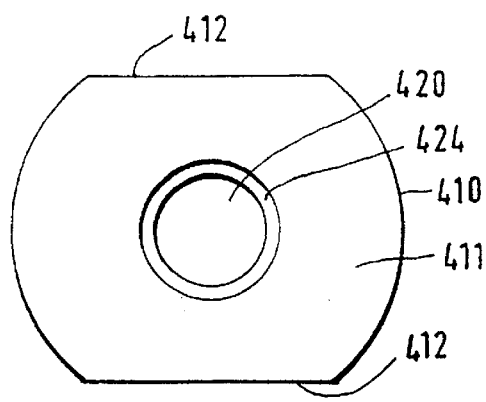
FIG. 4D: shows a top view of the protective cap of FIG. 4C.

FIGS. 4C and 4D

In an embodiment approximating to the shape of a tooth, the protective cap 400 comprises an approximately hemispherical basic body 410, the convex upper side 411 facing away from the tooth root. Here too, an axial through-bore 420 with a plurality of sections extends through the basic body 410. Towards the apical opening of the through-bore 420, the latter widens conically, so that a mating shoulder 421 which is complementary to the shoulder 10 of the implant is formed. Adjoining the mating shoulder 421, there rises the short cylindrical section 425, which merges into a narrowed cylindrical section 422. The screw head receiving part 423 with the conical seat 424 is located above the section 422. These protective caps 400 can also be prefabricated with different heights and diameters for the different spatial conditions in the mouth of patients. An initial adaptation to the surrounding teeth is achieved by means of flattened portions 412 on the basic body 410, which are to be positioned approximally.

Figure 5A:
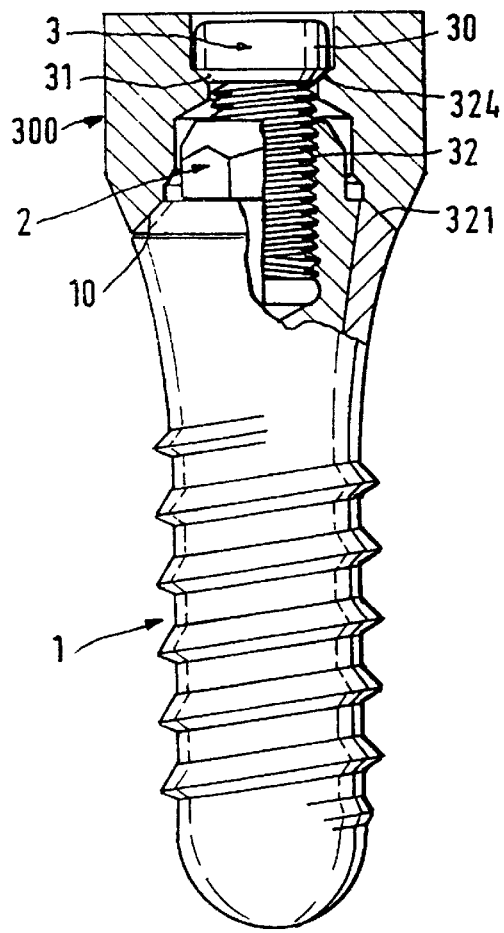
FIG. 5A: shows a full screw implant with a screwed-in polygonal secondary part and an attached protective cap in accordance with FIG. 4A, which is secured by an occlusal screw.
Figure 5B:
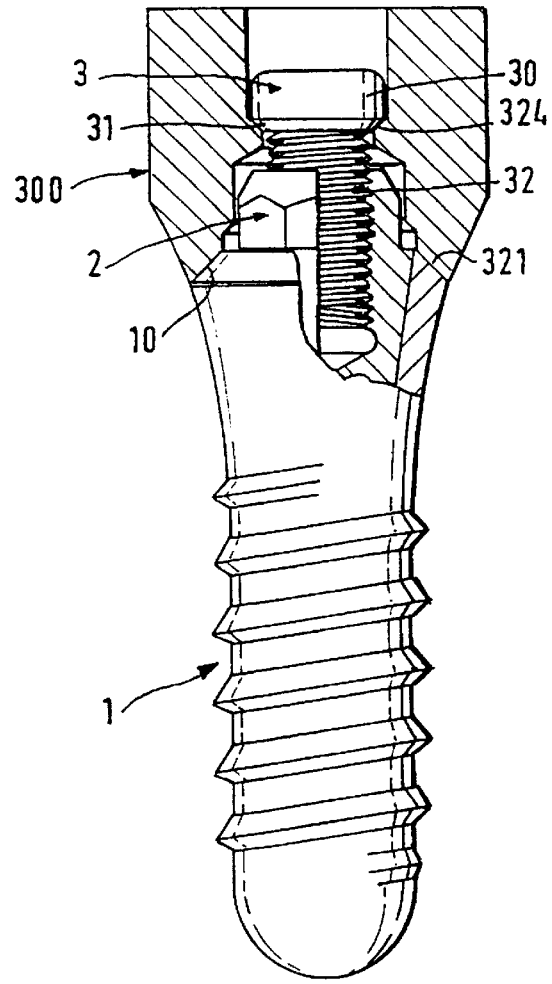
FIG. 5B: shows the representation of FIG. 5A, with a higher protective cap of increased diameter.

FIGS. 5A and 5B

The implant 1 is illustrated with a screwed-in polygonal secondary part 2 and an attached protective cap 300, which is secured by a conventional occlusal screw 3, the conical base 31 of the screw head 30 of the occlusal screw 3 being supported on the conical seat 324 inside the protective cap 300. The threaded shank 32 of the occlusal screw 3 penetrates through the through-bore 320 and engages into the polygonal secondary part 2. The mating shoulder 321 of the protective cap 300 fits on the shoulder 10 of the implant. The higher protective caps 300 project further above the shoulder 10 of the implant and the polygonal secondary part 2, so that the screw head 30 is countersunk more deeply in the through-bore 320.

Figure 5C:
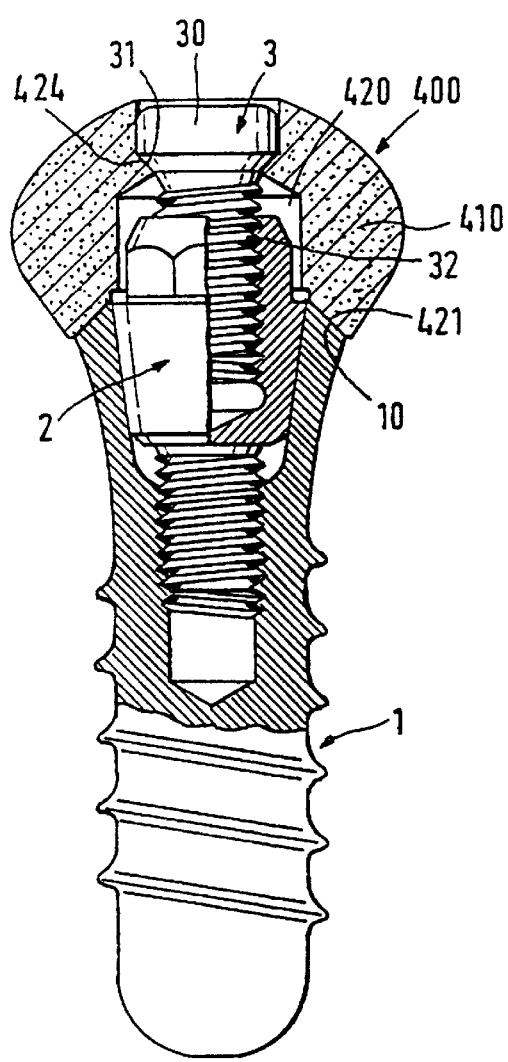
FIG. 5C: shows the representation of FIG. 5A with a protective cap in accordance with FIG. 4C, and FIG. 5D: shows the representation of FIG. 5C with a higher protective cap.
Figure 5D:
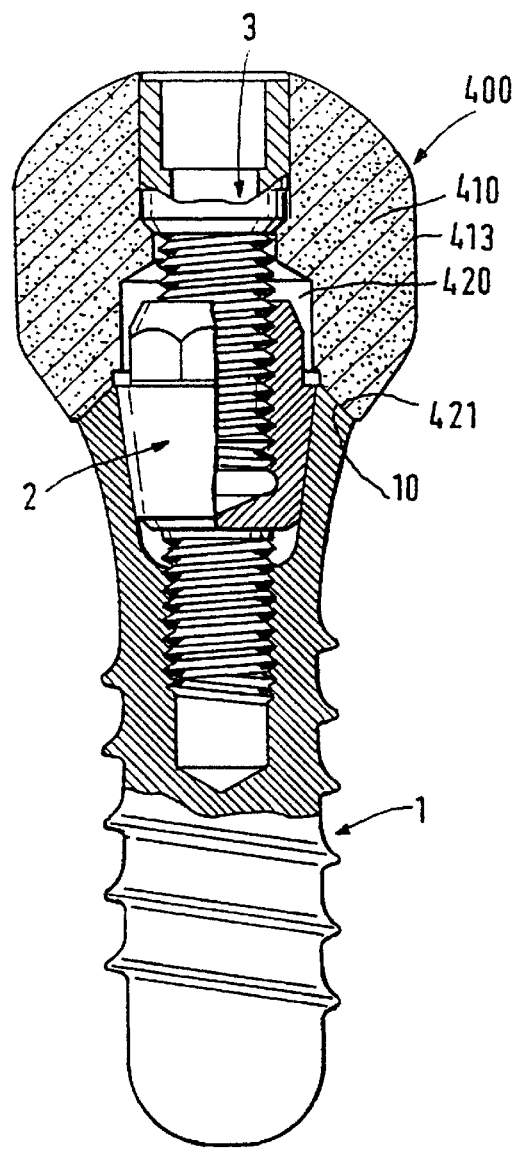

FIGS. 5C and 5D

The implant 1 is fitted with the screwed-in polygonal secondary part 2 and an attached protective cap 400, which is secured by means of the occlusal screw 3. The conical base 31 of the screw head 30 of the occlusal screw 3 is again supported on the conical seat 424 inside the protective cap 400. The threaded shank 32 of the occlusal screw 3 penetrates through the through-bore 420 and engages into the polygonal secondary part 2. The mating shoulder 421 of the protective cap 400 rests on the shoulder 10 of the implant practically without any gaps. The basic bodies 410 of higher protective caps 400 will advantageously have a straightened centre section 413.

Further structural variations can be carried out on the above-described healing cap 100 or the protective caps 300, 400. Expressly mentioned here are:

To simplify production, the bevel 116 may be provided so as to encircle the healing cap 100 completely.

The bevel 116 may have a configuration in which the opposite half-sides of the roof part 110 are bevelled partially or adjacently to one another.

Instead of the occlusal screw 200, other practicable positively-locking or non-positively-locking means may also be used to fix the healing cap 100 on the implant 1, which may make the through-bore 130 superfluous.

The pin 120 could be shortened to such an extent that, in the transition to the mating shoulder 115, a centering bead 118 is formed (see FIG. 1A).

The healing cap 100 may in be of round or oval configuration or be configured with additional bulges and indentations.

The engagement contour 212 in the screw head 210 may have a cross slot, a polygon or a conventional non-rotationally symmetrical contour.

Furthermore, it is possible to produce the basic body 310, 410 of the protective cap 300, 400 from plastic which can be burnt out or is composite-compatible and thus to preform anatomically the basic body 310, 410 further.

We claim:

1. A healing cap for an intraossally positioned dental implant, comprising:

a roof part having a top surface, an outer circumferential surface, a lower circumferential shoulder edge, and a conical mating shoulder located on an underside of said roof part, said mating shoulder being of a shape complementary to a shoulder of the implant;

a bevel depending from said top surface and positioned on said circumferential surface and extending partly therearound, said bevel ending above said shoulder edge;

a chamfer extending downward from said bevel to said shoulder edge;

a through-bore extending axially through said healing cap; and a screw inserted into said through-bore, said screw securing said healing cap on the implant.

2. A healing cap according to claim 1, wherein said bevel extends over approximately half said circumferential surface, said bevel tapering smoothly downwards.

3. A healing cap according to claim 1, wherein said bevel extends completely around said circumferential surface.

4. A healing cap according to claim 1, further comprising an axial pin depending from said underside of said roof part, said axial pin including an end portion having a shape complementary to an inner contour of the implant, said conical mating shoulder of said roof part extending from said circumferential shoulder edge towards said axial pin in the form of a circular ring.

5. A healing cap according to claim 4, wherein said axial pin has a frustum-like shape, which creates a centering bead at a transition to said mating shoulder.

6. A healing cap according to claim 1, wherein said through-bore includes a screw head receiving part ending in a conical seat and an internally threaded section extending downward from said conical seat.

7. A healing cap according to claim 1, wherein said top surface includes a rounded transition to said circumferential surface, said rounded transition having a convex contour.

8. A healing cap according to claim 1, wherein said screw includes a screw head and a screw shank having an unthreaded part and a threaded part, said unthreaded part depending from said screw head, said threaded part depending from said unthreaded part and having a larger diameter than said unthreaded part.

9. A healing cap according to claim 8, wherein said screw head includes:

a recessed contour in an upper side thereof, said contour sized and shaped to receive a turning tool; and a conical base on a lower side thereof, said conical base being positioned above said screw shank.

* * * * *